(12) United States Patent
Donovan

(10) Patent No.: US 8,439,873 B1
(45) Date of Patent: May 14, 2013

(54) CATHETER WITH POSITION INDICATOR

(76) Inventor: Gail Marie Donovan, Cincinnati, OH (US)

( * ) Notice: Subject to any disclaimer, the term of this patent is extended or adjusted under 35 U.S.C. 154(b) by 161 days.

(21) Appl. No.: 12/928,599

(22) Filed: Dec. 15, 2010

Related U.S. Application Data

(60) Provisional application No. 61/284,307, filed on Dec. 17, 2009.

(51) Int. Cl.
*A61M 5/32* (2006.01)
*A61M 5/00* (2006.01)
*A61M 31/00* (2006.01)

(52) U.S. Cl.
USPC ............ 604/117; 604/116; 604/174; 604/508

(58) Field of Classification Search .................. 604/180, 604/523, 174, 177, 532, 116, 117, 500, 508; 283/81; 600/585
See application file for complete search history.

(56) References Cited

U.S. PATENT DOCUMENTS

| | | | | |
|---|---|---|---|---|
| 6,511,471 | B2 * | 1/2003 | Rosenman et al. | 604/528 |
| 7,817,498 | B1 * | 10/2010 | Hinckley | 368/10 |
| 2006/0129103 | A1 * | 6/2006 | Bierman et al. | 604/174 |
| 2008/0255475 | A1 * | 10/2008 | Kondrosky et al. | 600/585 |

OTHER PUBLICATIONS

Pettit, Janet, Trimming of Peripherally Inserted Central Cathters: The End Result, Journal of the Association for Vasucual Access, vol II, No. 4, pp. 1-6, 2006.*

* cited by examiner

*Primary Examiner* — Bhisma Mehta
*Assistant Examiner* — Lauren M Peng
(74) *Attorney, Agent, or Firm* — Charles R. Wilson

(57) ABSTRACT

A peripherally inserted central venous catheter having a position indicator is used in a method of detecting movement of a catheter tip within a patient's superior vena cava. The PICC comprises a catheter having a proximal end with distance marks at measured intervals, an anchor wing system secured to the catheter's proximal end, at least one extension leg secured to the anchor wing system and the position indicator attached to the extension leg. The position indicator has an area for marking a distance signifying an initial external length of catheter which extends from the point the catheter enters the patient to the point it is attached to the anchor wing and/or marking an initial full length or the internal length of catheter which is fully within the patient. Any movement of the catheter's tip is detected by comparing the current external distance mark with the initial external distance mark.

1 Claim, 3 Drawing Sheets

CATHETER WITH POSITION INDICATOR

This application claims the benefit of U.S. Provisional Application No. 61/284,307, filed Dec. 17, 2009.

FIELD OF THE INVENTION

This invention relates to a central venous catheter having an indicator to show the exact position of catheter placement in a patient. More particularly, the invention relates to a central venous catheter with a position indicator whereby the initial length of a catheter inside and outside a patient's vein are readily known. It further relates to a method of monitoring initial placement of the central venous catheter's tip within the superior venous cava to determine when corrective action is needed.

BACKGROUND OF THE INVENTION

Central venous catheters are widely used in the medical field. Some current drugs are caustic or irritating to lower arm veins which have smaller diameters. The standard of choice now is to deliver medications into larger blood vessels located in the central portion of the patient's chest. Thus, a catheter is advanced into the largest vein in the body, called the superior vena cava. Central lines are precisely placed at the junction of the superior vena cava and the heart's atrium.

In particular, a peripherally inserted central venous catheter (PICC or PICC line) is initially inserted into a peripheral vein, normally in the upper arm of the patient. It is then advanced through larger veins towards the heart for a prescribed distance. PICCs are intended to remain in place for extended periods, e.g. from a few days up to a few years. They provide a means for long-term chemotherapy regimens, extended antibiotic therapy, total parenteral nutrition, extended venous access, and blood sampling.

It is most important that a catheter tip, where introduced fluids exit the PICC and enter the body, be precisely positioned in the body. The catheter's tip must be positioned in the lower one-third of the superior vena cava, close to a junction of the superior vena cava and the heart's right atrium. Ultrasound, chest radiographs, and fluoroscopy techniques are used by trained nurses or doctors to aid in insertion of the catheter and to confirm that its tip is properly positioned. There are only a few centimeters of space in the superior vena cava vessel where it can safely sit. This is well accepted and is attainable provided proper care is taken by trained personnel, including a specially trained PICC nurse who first performs the procedure and a radiologist who confirms the position of the catheter's tip. The initial positioning of the catheter tip is critical, but follow-up monitoring is just as important.

The PICC must remain in its exact place once properly positioned or at least be readily repositioned if need be. Any catheter tip movement can lead to an enormous increase, e.g. 60% to 70% in the rate of thrombosis, infection, heart dysrythmias and perforation, or catheter dysfunction. Simply taping the catheter to the patient at its entry point into the body is not permissible because of the increased risk of infection at the site. Because a catheter's length inside the patient's body is a specific fit to their unique vasculature, all measurements are different. Generally, there are several centimeters of catheter left outside the upper arm, configured in an upward loop to avoid the bend in one's arm. This loop of catheter, in turn, leaves a degree of "play" or instability related to its original position. The catheter exits the vein through a tiny cut in the arm and is held in place only by a sticky clear occlusive sterile dressing. Close monitoring and meticulous care are required to ensure the catheter does not move. Catheter tip movement can be caused by several factors. A patient's natural body movements is one cause. Perspiration, moisture or blood under the dressing, all of which loosen the dressing's adhesive, is another cause. Strenuous physical activity of the upper extremities and poor technique during dressing changes are some other examples. Considering a patient may be required to keep a PICC line in place continually for weeks and even months at a time, it should not be surprising that inadvertent movements and bumpings that affect the catheter's tip placement will occur. Further, multiple dressing changes by different clinicians, possibly at different hospital units and other medical facilities all present opportunities for the initial precise positioning of the catheter tip to be totally negated.

There often is no continuity in the maintenance of the PICC's original position because no visual cue exists. With the plethora of activity surrounding a patient and the unfortunate fact that hospitals do not use "position indicators" or any type of label to aid in monitoring catheters (even those residing near one's heart) the safety of PICC lines are diminished. It is a simple fact the catheter tip frequently moves and the movement goes undetected. Poor catheter management leads to unwanted chemical and mechanical irritation of a vessel which triggers the clotting process leading to thrombosis and catheter-related infections.

Another potential problem with PICC's is the fact it is known that the catheter line can sometimes simply break off while in the patient's body. It is imperative that when a PICC procedure is completed and the catheter line retracted that the full length be retracted. Any broken-off portion which remains behind can ultimately cause severe damage to the patient. There is currently not a measure in place which ensures that no portion of the catheter line has been left behind. Referring to the original medical chart would help, but the chart is often unavailable to the clinician.

The lengths of catheter within the body and outside the body when a PICC procedure is first performed is recorded on the patient's medical chart. Regardless, the information is of little value when there are frequent follow-up facilities involved and many different medical personnel that can be involved over a course of possibly months. All the while clotting formation, infection, and catheter dysfunction in the patient due to catheter movement is possible.

There are no indicators to compare the present location of the tip of the catheter in the vessel with its original safe position within the vein. Simply looking at the exterior portion of a PICC is of no avail to determining if it has moved further into or out of the patient's body. Basically, clinicians today employ guesswork when maintaining these lines. This places an individual at great risk, sometimes even life threatening.

What is needed is an improved PICC which allows trained medical personnel to detect movement and immediately know if corrective action is needed. In response to this need, there has now been developed a position indicator designed specifically for use with central venous catheters and a method of monitoring safe use of the central venous catheter. It is especially for use with PICCs. This is because PICCs are placed in a patient's arm where a lot of movement takes place with a consequent enhanced chance for catheter movement.

SUMMARY OF THE INVENTION

A peripherally inserted central venous catheter includes a position indicator for use in a method of monitoring movement of the catheter over an extended time period. The central venous catheter comprises (a) a catheter with distance marks extending at set intervals from a proximal end towards a distal end, (b) an anchor wing system for temporary attachment to a patient and wherein the system is secured to the proximal end of the catheter, (c) at least one extension leg having a proximal terminus which is accessible for delivering fluids directly to the patient's superior vena cava through the catheter, and (d) the position indicator attached to the extension leg. The position indicator has an area for marking a distance signifying an initial external length of catheter and optionally for marking an initial internal length of catheter.

DETAILED DESCRIPTION OF THE INVENTION

The peripherally inserted central venous catheter (PICC) of the invention and a method of monitoring initial placement of the PICC in a patient's superior vena cava for movement using the PICC of the invention are described in detail in the following paragraphs. The PICC is primarily used for dispensing medications through the catheter directly into a patient's superior vena cava. The medications can be part of a long-term chemotherapy regimen, extended antibiotic treatment, or long-term medicinal regimen. The PICC can as well be used for supplying total parenteral nutrition to the patient, providing a means of venous access, and withdrawing blood for testing.

Figure 1:
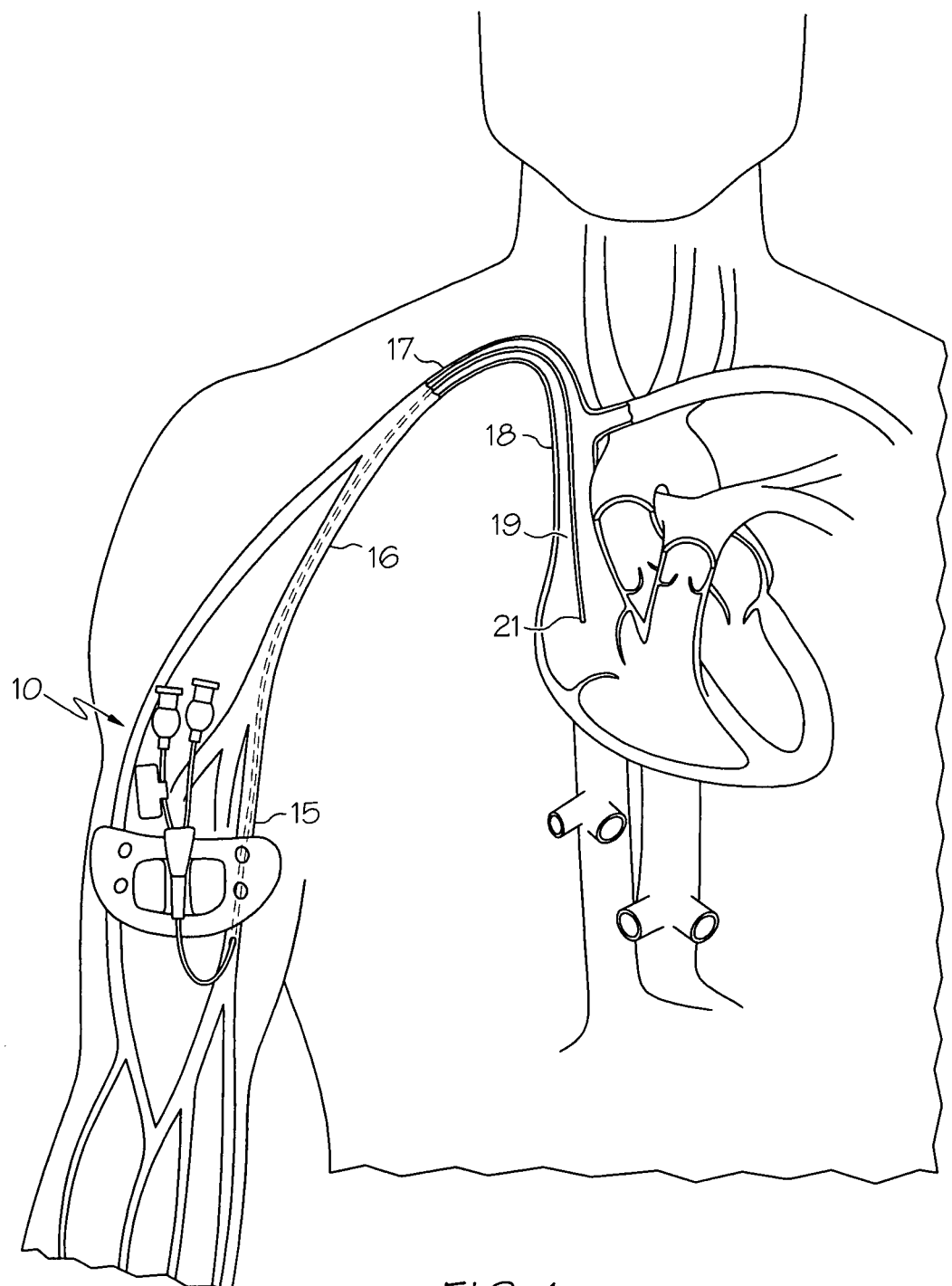
FIG. 1 is a schematic of an upper portion of human body showing a heart with associated veins and the peripherally inserted central venous catheter of the invention.

With reference to FIG. 1, there is depicted an upper portion of a human body in schematic form with the PICC 10 of the invention in position. Components of the PICC 10 are described in detail below as is a method of monitoring catheter tip placement using the PICC 10. Briefly and with reference to FIG. 2, the PICC 10 comprises a catheter 11, an anchor wing system 12, at least one extension leg 13, and a position indicator 14. The catheter 11 as evident in FIG. 1 enters the human body's circulatory system in a basilic vein 15, and then extends through it, an axillary vein 16, a subclavian vein 17, a brachiocephalic vein 18, and ultimately a superior vena cava vein 19. As evident, the veins progressively get larger in diameter.

Again with reference to FIG. 2, the PICC 10 includes a catheter 11 having a length sufficiently long to reach from the point of insertion into the patient to the superior vena cava of the patient. Normally, the catheter's length is about thirty-five centimeters to about fifty-five centimeters (cm). This length is adequate for normal sized patients. As discussed below, the catheter is shortened during use when it is evident an excessive length will extend outside the patient's body and perhaps hinder its use.

The catheter 11 has a proximal end 20 and a distal end 21. It further has distance marks 22 at measured intervals starting at the proximal end and continuing at least past the point of entry into a patient and preferably the entire catheter length. As shown, the distance marks 22 are a line on top of the catheter and are spaced at one cm intervals. It should be understood other measured intervals can be line marked as well as number marked, e.g. by 1, 2, 3, 4, 5, etc.

Again with reference to FIG. 2, the catheter 11 is secured at its proximal end 20 to an anchor wing 23 of the anchor wing system 12. The anchor wing system 12 is conventional. Other designs are known and are usable in the invention. It serves as a junction point for the catheter 11 with the extension leg 13. It further serves as a means by which the PICC 10 can be temporarily attached to the patient. One means of attachment is adhesive on the system's underside. As shown, the anchor wing system includes the anchor wing 23 permanently attached to a foam pad 24. The foam pad has adhesive on its underside. Adhesive tape can as well be used.

Figure 2:
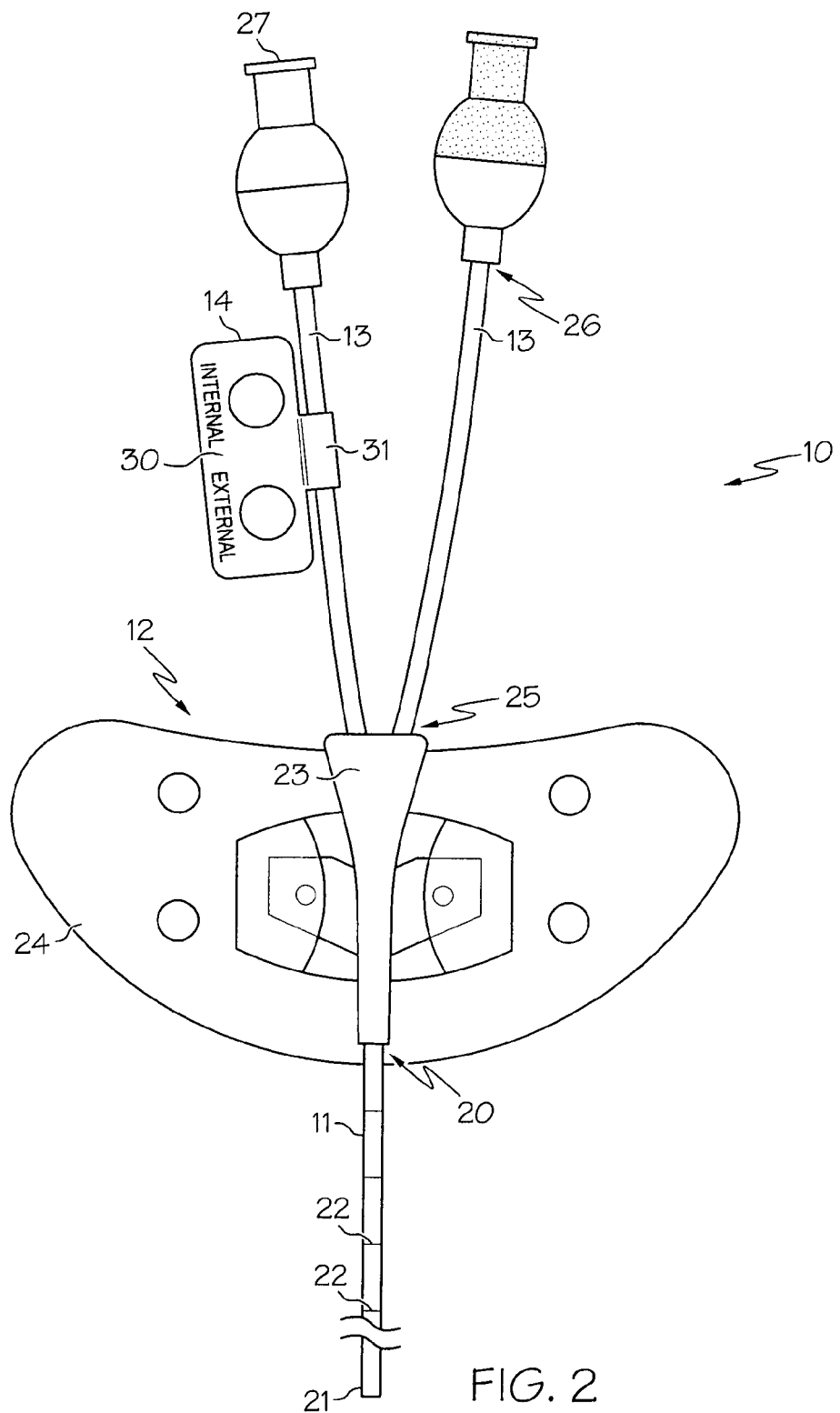
FIG. 2 is an isolated plan view of the peripherally inserted central venous catheter of FIG. 1.

Still with reference to FIG. 2, the PICC 10 further includes at least one extension leg 13, preferably from one to three extension legs, securely attached at a distal end to the anchor wing 23 of the anchor wing system 12. Two extension legs 13 are shown, each attached at a distal end 25. A proximal end 26 of each extension leg has a catheter hub 27 which is used to access a tubular delivery cavity extending through a lumen within the extension leg and the catheter so as to be in fluid communication.

One embodiment of the position indicator 14 of the invention is shown in FIG. 2 and described below. The position indicator 14 has a marking member 30 and an attaching tab 31 extending from one edge thereof. The position indicator 14 is shown as having a rectangular-shaped marking member 30 and a rectangular-shaped attaching tab 31. The marking member can as well be square-shaped, circular-shaped, etc. Generally, it is at least about two centimeters in its minimum length to allow marking space. Its maximum length is determined primarily by convenience in use purposes, with less than about three centimeters being preferred. The attaching tab 31 extending from one edge of the rectangular-shaped marking member 30 is dimensioned to conveniently and securely attach to an extension leg 13 as shown or some other exterior portion of the PICC. It is positioned on the extension leg outside any sterile occlusive dressing applied to the patient to avoid site contamination. The attaching tab 31 is as small as possible so as to minimize the amount of the extension leg's interior which is blocked from view. Alternatively, the attaching tab can be wider provided it is transparent or has a cut-out so that the extension leg's interior is viewable. This is important to the nurse or doctor so that a brisk flow of blood into the extension leg can be observed. Brisk blood return when aspirated is one barometer of the catheter's proper tip position and full functionability.

Figure 3:
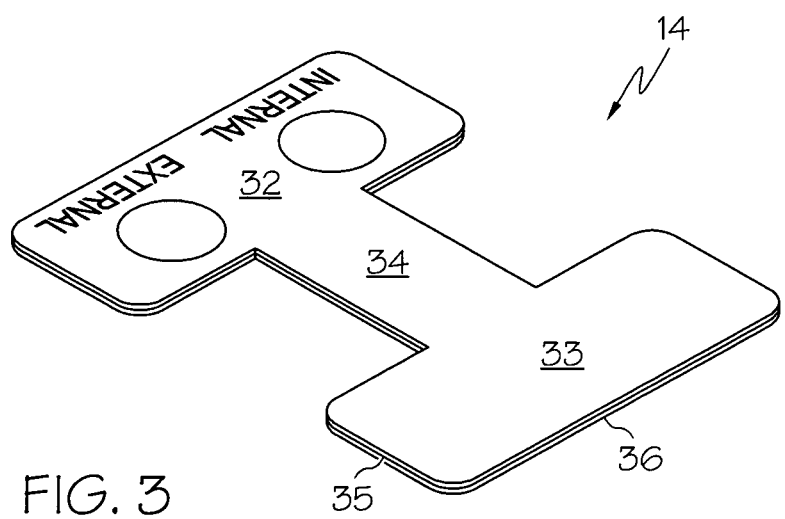
FIG. 3 is a view in perspective of a position indicator found on the central venous catheter of FIG. 2.

The position indicator 14 is best seen in FIG. 3 prior to its placement on the PICC. The marking member includes a first thin flat body 32 and a second thin flat body 33 connected by a bridge 34. It is made from a polymeric film, though could be made of coated paper or any other suitable material. A thin foam-like film is preferred for reduced skin abrasion for enhanced patient comfort. A back side of the marking member has an adhesive 35 and a removable cover 36. In use, the cover 36 is removed to expose the adhesive 35. The marking member is then positioned over an exposed portion of the PICC, e.g. an extension leg as shown and folded together so that the first and second thin flat bodies mate to permanently remain together.

As apparent, space on the thin flat body 32 is available for marking the external length of exposed catheter unique for the patient. This is the length of catheter from the point where it enters the patient to its proximal tip where it meets the anchor wing. Space is also available for marking the internal length of catheter. Knowing the original internal length is important when the catheter is removed from the patient to determine if the full catheter is being removed. Catheters have been known to break off and unknowingly be left behind.

Briefly, the catheter portion of the PICC is run through a peripheral vein and continues through different veins to the superior vena cava. Once its tip is properly positioned, the anchor wing system of the PICC is secured to the patient and sterile dressing applied. The portion of the catheter extending outside the body is never secured to the patient, with a consequent possibility for some movement. Next, the length of the external portion of the catheter is measured and recorded in the space provided on the marking member of the position indicator. The internal length is determined by subtracting the external length from the total length and so recorded in the space provided. The position indicator can be secured to the PICC either before or after the measurements and recordings are made.

Now in greater detail, the central venous catheter of the invention is used in a series of steps to monitor the initial exact placement of a catheter tip to ensure that any tip movement is detected. The monitoring method of the invention includes the following essential steps:

(a) Initially, a site on the patient's arm is selected for insertion of the catheter tip of the PICC. Normally, the site selected is to gain access to a basilic vein because of its size and the fact it has the most direct route into superior vena cava.

(b) An estimate is made of the length of catheter needed in the procedure. This involves measuring from the selected site up the arm and down to the appropriate location of patient's superior vena cava. The length of catheter needed is equal to the approximate length from the point the catheter attaches to the anchor wing of the central venous catheter to the entry point on the patient and finally to the superior vena cava of the patient.

(c) The catheter is cut if need be to reach the estimated measured length.

(d) The selected site of the patient is thoroughly cleaned and sterilized to reduce the risk of infection.

(e) An entry point is found and the catheter is inserted into the basilic vein. A hollow needle and guide wire are used in part of the procedure in accord with known procedures.

(f) The catheter tip is advanced through the basilic vein, the axillary vein, the subclavian vein, the brachiocephalic vein, and finally positioned in a lower one-third of the superior vena cava, close to a junction of the superior vena cava and the heart's right atrium.

(g) An x-ray is taken to verify the position of the catheter's tip, with any positioning adjustments made as needed.

(h) The catheter's entry point is gauzed to minimize bleeding and form a sterile occlusive dressing. The anchor wing system is next temporarily adhered to the patient to anchor the extension legs.

(i) The external length of the catheter extending from the anchor wing to the point it enters the patient is ascertained.

(j) The position indicator is marked with the external length of the catheter. The internal length of the catheter and other pertinent information can as well be marked on the position indicator.

(k) The position indicator is securely attached to a part of the central venous catheter, external from the entry point and outside the sterile occlusive dressing. It is attached to the extension leg.

(l) The catheter tip's exact placement in the superior vena cava as initially determined is periodically monitored by noting the current external length of catheter from the anchor wing to the point of patient entry and comparing it with the external distance noted on the position indicator. If there is a difference, action is promptly undertaken to correct the placement.

There can be other steps taken in the above described method, primarily to ensure a clean safe environment to reduce the risk of infection and to ensure the comfort of the patient during the method. Such steps are performed as desired.

The position indicator is not restricted to that shown. Other means of attaching the marking member to a PICC can be used. For example, the position indicator can have a plastic coated wire extending from the marking member with a length sufficient to wrap around an extension leg and twist around itself to restrict removal. An expandable elastomeric ring permanently attached to the marking member can be slid over the catheter hub and remain in place. Still other attachment means can be used. Still other position indicators that accomplish my objective are contemplated.

Having described the invention in its preferred embodiment, it should be clear that modifications can be made without departing from the spirit of the invention. It is not intended that the words used to describe the invention nor the drawings illustrating the same be limiting on the invention. It is intended that the invention only be limited by the scope of the appended claims.

I claim:

1. A method of monitoring initial placement of a peripherally inserted central venous catheter in a patient's superior vena cava for periodically safely dispensing fluids over an extended time period wherein the central venous catheter includes a catheter about thirty-five cm to about fifty-five cm in length with distance marks at measured intervals extending towards a distal end, an anchor wing system securely attached to a proximal end of the catheter and at least one extension leg having an accessible proximal terminus and a distal terminus securely attached to the anchor wing system and in fluid communication with the catheter, said method comprising the steps of:

a. selecting an entry site on the patient in close proximity to a basilic vein;

b. estimating a total length of catheter needed to extend from a point of attachment to the anchor wing system to a lower one-third of the superior vena cava of the patient and wherein the total length of catheter needed comprises an initial external length which extends from the point of attachment to the anchor wing system to an entry point on the patient and an initial internal length which extends from the entry point on the patient to the lower one-third of the superior vena cava of the patient;

c. optionally cutting the catheter of the central venous catheter to the total length estimated needed;

d. inserting the catheter of the central venous catheter through the entry point on the patient so that a tip of the catheter extends to the lower one-third of the patient's superior vena cava;

e. confirming the position of the catheter's tip within the patient's superior vena cava;

f. attaching the anchor wing system to the patient;

g. determining the initial external length of catheter extending from the anchor wing system to the point it enters the patient;

h. marking a position indicator with the initial external length of the catheter and, optionally, the initial internal length of the catheter;

i. attaching the position indicator onto an external portion of the central venous catheter; and j. periodically comparing a subsequent external length of catheter extending from the anchor wing system to the point it enters the patient with the initial external length marked on the position indicator.

* * * * *